United States Patent [19]

Hayden et al.

[11] 4,094,889
[45] June 13, 1978

[54] RESTORING SELECTIVITY OF ALKALI METAL PROMOTED SILVER CATALYSTS AND PRODUCTION OF OLEFINE OXIDES

[75] Inventors: Percy Hayden; Richard William Clayton, both of Middlesbrough, England

[73] Assignee: Imperial Chemical Industries Limited, London, England

[21] Appl. No.: 772,280

[22] Filed: Feb. 25, 1977

[30] Foreign Application Priority Data

Mar. 5, 1976 United Kingdom ............... 8897/76

[51] Int. Cl.$^2$ .................... C07D 301/10; B01J 23/96
[52] U.S. Cl. ............................... 260/348.34; 252/420
[58] Field of Search ............... 252/420, 426, 416; 260/348.5 R, 348.34

[56] References Cited

U.S. PATENT DOCUMENTS

| 2,194,602 | 3/1940 | Law et al. ............................ 252/476 |
| 2,479,883 | 8/1949 | West et al. ........................... 252/420 |
| 3,962,286 | 6/1976 | Antonelli et al. ............. 260/348.5 R |
| 4,007,135 | 2/1977 | Hayden et al. ..................... 252/476 |

*Primary Examiner*—Winston A. Douglas
*Assistant Examiner*—P. E. Konopka
*Attorney, Agent, or Firm*—Cushman, Darby & Cushman

[57] ABSTRACT

The selectivity of unstable alkali metal promoted silver containing olefin oxide production catalysts is restored by wetting them.

11 Claims, No Drawings

RESTORING SELECTIVITY OF ALKALI METAL PROMOTED SILVER CATALYSTS AND PRODUCTION OF OLEFINE OXIDES

This invention relates to the production of olefine oxides.

In the oxidation of olefines especially ethylene to the corresponding olefine oxides by reacting them with oxygen in the presence of alkali metal promoted silver containing catalysts it is sometimes found that the catalysts are unstable especially if they are highly selective in that they lose selectivity with time, i.e. a smaller proportion of the converted olefine is converted to the desired olefine oxide.

This invention provides a process of restoring selectivity to unstable alkali metal promoted silver containing catalysts for the oxidation of olefines to olefine oxides which have lost selectivity in that reaction, which comprises wetting the catalyst with water and drying it.

By "unstable" we mean a catalyst which after any initial conditioning period exhibits a substantial decline in selectivity (for example a decline of 0.2% or more or 1% or more, for example 3, 4 or 5% or more, per month) in normal use.

It is preferred that the alkali metal should be rubidium cesium or potassium or more preferably sodium.

The catalyst may be wet with water by contacting it with liquid water, by wetting it with wet steam or by absorbing water into the catalyst from steam in the vapour phase. It is preferred to use liquid water or in some cases for the sake of convenience, wet steam.

It is preferred that the amount of water absorbed into the catalyst should at least for part of the time approach or be equal to the water porosity of the catalyst. If desired the volume of water to which the catalyst is exposed may exceed the water porosity but it is desirable in this case that excess water should not be discarded but should be evaporated in contact with the catalyst in order to avoid loss of catalyst components. Contact with water may be carried out however at any convenient temperature for example from 20° to 300° C. Suitably the water is removed by evaporation at a temperature of 100°–300° C.

The silver may be present as silver but is preferably present at least in part as silver oxide for example as a film of silver oxide on silver particles. It is preferred that at least 50% of the silver particles be present as discrete particles adhering to a support and having equivalent diameters of less than 10,000A, preferably in the range 200 to 10,000A. By "equivalent diameter" is meant the diameter of a sphere of the same silver content as the particle. The dimensions of the silver particles may be determined by scanning electron microscopy.

It is preferred that the silver and alkali metal should be supported on a porous heat resisting support. Such supports are suitably alumina, silicon carbide, silica, zirconia or silica/alumina supports, α alumina or silicon carbide being preferred. The support is preferably a preformed porous heat resisting support into which the other catalyst components are introduced by impregnation. It preferably has a surface area in the range 0.04 to 10$m^2$/g, preferably 0.05 to 3$m^2$/g and more preferably 0.1 to 1.5$m^2$/g but especially 0.2 to 0.6$m^2$/g as measured by the Brunauer Emmett and Teller method, an apparent porosity as measured by the mercury absorption method of at least 20%, preferably 30–65% and more preferably 40–60% for example 45–55% and median pore diameters of 0.3 to 15 microns, preferably 1–15 microns as measured by the mercury prosoimetry method.

The said amounts of alkali metal are in excess of any present in the preformed supports.

The catalyst preferably comprises 3–15% and more preferably 6–12% by weight of silver.

The preformed support may be impregnated with a solution comprising 3–50% of silver by weight and a nitrogen-containing ligand for example acrylonitrile, ammonia, and/or an amine for example pyridine, hydroxylamine, or vicinal alkyl diamines having from 2–4 carbon atoms for example ethylene diamine optionally together with vicinal alkanolamines. The alkali metal may be introduced with the silver as a compound soluble in the silver solution or by a separate impregnation step before or after introduction of the silver.

The alkali metal may be introduced as a halide for example a chloride, sulphate, nitrate, nitrite carboxylate or as any other suitable compound. It is preferred that it should be introduced as a hydroxide, carbonate, bicarbonate, nitrate, nitrite, formate, acetate, oxalate, citrate, or lactate.

It is preferred that the catalysts should be substantially free from any alkaline earth metal.

It is desirable that silver should be deposited as discrete particles throughout substantially all of the available surface (inter alia within the pores) of the support as well as on the superficial surface. In order to ensure that as much of the silver and promoter is in the pores of the support as possible rather than being deposited on the external surface of the support it is preferred that the total amount of solution used should be such that it is substantially entirely absorbed into the support rather than an excess being left in contract with it. Any surplus solution may alternatively be drained off prior to drying the solid. The silver compound may be decomposed by heating the impregnated support to a temperature of 200°–400° C, preferably 200°–350° C.

The preferred alkali metal is sodium. It is preferred that the sodium content should be in the range $10^{-2}$ to 10% by weight of the catalyst. It is preferred that the sodium content should be in the range $3 \times 10^{-5}$ to $5 \times 10^{-1}$ grams of sodium per sq. meter of surface area of support. The preferred content of potassium is in the range $2 \times 10^{-2}$ to $3 \times 10^{-5}$ grams per sq. meter of surface area of support. The preferred concentration of rubidium is in the range of $1 \times 10^{-2}$ to $3 \times 10^{-5}$ grams/sq. meter of surface area support and of cesium is in the range $5 \times 10^{-3}$ to $3 \times 10^{-5}$ g/$m^2$ of surface area of support.

If desired boron may be present for example as a water extractable boron compound, suitably in an amount in the range $5 \times 10^{-4}$ to $1 \times 10^{-5}$ g/$m^2$ of the surface area of support and/or a water extractable silicate or aluminate may be present in an amount expressed as silicon or aluminium respectively in the range $1.5 \times 10^{-3}$ to $1 \times 10^{-5}$ g/$m^2$ of surface area of support.

The conversion of ethylene to ethylene oxide using the catalysts of the invention may be carried out in a conventional manner. Pressures of from 1 to 35 bars absolute may be employed. The temperature is suitably in the range 190° to 270° C, and preferably 210° to 245° C. In general, a diluent, for example methane, is present in proportions of, for example 10 to 40% by weight. Generally 5 to 70% for example 50 to 70% of ethylene is converted and unconverted ethylene is recycled. Oxygen may be supplied, for example, in the form of air or of commercial oxygen. Carbon dioxide is generally also present. A reaction modifier, for example ethylene dichloride, may be used.

It is generally observed that in the production of propylene oxide conversion rate rises with total pressure of the reacting gases, but more particularly it rises as the partial pressure of oxygen is increased. Furthermore it is generally observed that the selectivity of the oxidation to propylene oxide rises as the ratio of oxygen pressure to propylene pressure is increased. It is preferred that the molar ratio of oxygen to propylene is in the range of about 0.05 to about 100, and more preferably in the range 0.1 to 5.

Partial pressures of propylene of 0.3 to 50 bars may be used. The total pressure may be in the range of from 1-100 bars absolute. The molar ratio of oxygen to propylene may be in the range 0.05 to 100. The partial pressure of oxygen may be in the range 0.02 to 10 bars, preferably 0.5 to 5 bars, and more preferably 1 to 4 bars, and may be supplied, for example in the form of air or as commercial oxygen. A diluent or a mixture of diluents, for example helium, nitrogen, argon, methane and carbon dioxide, may be present in molar proportions of up to 30:1, but preferably between 0.5:1 and 5:1 relative to the total number of moles of propylene and oxygen taken together. The temperature is suitably in the range 200°0 to 300° C, and preferably in the range 220° to 280° C. Contact times should be suficient to convert 0.05 to 50%, for example 1 to 20% of propylene and unconverted propylene is recycled. Carbon dioxide may also be present. A reaction modifier, for example ethylene dichloride or vinyl chloride, may be used to improve catalyst performance and to minimise the formation of hot spots in the catalyst.

EXAMPLE 1

A commercial α-alumina catalyst support material supplied by Norton Ltd., number SA5500 (surface area $0.3 m^2 g^{-1}$) was crushed and sieved to give pellets with diameters in the range 0.42 to 1.00mm.

Three silver catalysts for the oxidation of olefines were prepared and tested as follows:-

A solution of silver acetate was prepared by dissolving 5.8g reagent grade silver acetate in 8ml aqueous ammonia (SG 0.880). This solution was filtered and 1.0 ml of ethanolamine, 0.21 g of sodium acetate and 0.003 g of sodium tetraborate decahydrate added. The resulting solution was added dropwise with stirring to 30 g of the support material which was continuously stirred.

The resulting support, impregnated with the solution, was heated in an air purged oven for 4 hours. During this time the oven temperature was raised from 100° C to 300° C at a rate of 0.8° C per min.

The resulting catalysts (Catalyst A) contained 8% silver by weight and 0.12% sodium by weight.

20 g of each catalyst was loaded into a glass reactor (internal diameter 13mm) contained in an air circulated thermostatically controlled oven. A gas stream containing 30% $C_2H_4$, 8% $O_2$, 62% $N_2$ and 4 ppm ethylene dichloride was passed over the catalysts at 1 bar pressure and a gas hourly space velocity of 200 $hr^{-1}$.

Each catalyst was used at 240° C. The selectivity of the fresh catalyst was 92% but, over the course of about 30 days of continuous use, the selectivity diminished to 80%.

The discharged catalyst was impregnated with 7 gm of water and the resulting damp solid was heated in an air purged oven for 4 hours during which time the oven temperature was raised from 100° C to 300° C at a rage of 0.8° C per min. This provides Catalyst A.

A second discharged catalyst was contacted in a pressurised reactor at 173° C with a nitrogen-water mixture (30(NTP)liters per hour) for 2 hours. The nitrogen-water mixture was formed by saturating a nitrogen stream with water at 180° C. Following exposure to water, the catalyst was heated in a stream of air at atmospheric pressure for 4 hours at 300° C. The sequences of exposure to water and of drying was repeated. This provides catalyst B.

In a comparative experiment a third discharged catalyst was heated in an air-purged oven for 4 hours during which time the oven temperature was raised from 100° to 300° C at a rate of 0.8° C per min. This comparative procedure provides catalyst X. Catalyst A, B and X were again used in the synthesis of ethylene oxides: the selectivities of these treated discharged catalysts were 91%, 91.5% and 81% respectively.

EXAMPLE 2

A catalyst for the oxidation of olefines was prepared and tested as follows:

5.8g of reagent grade silver acetate was dissolved in the minimum amount of aqueous ammonia required to give complete dissolution. 0.24g of sodium acetate were added and the solution was made up to 8 ml by the addition of water. This solution was used to impregnate 30g of the support material used in example 1.

The resulting support, impregnated with the solution, was heated in an air purged oven for 3 hours at a temperature of 290° C.

The resulting catalyst contained 8% silver by weight and 0.12% sodium by weight.

A 20g sample of this catalyst was tested as in example 1 and the selectivity measured at a pressure of 1 bar, a temperature of 240° C and a gas hourly space velocity of 200 $hr^{-1}$. The selectivity of the fresh catalyst was 91% but over a period of 20 days this fell to 84%.

This decayed catalyst was discharged and impregnated with 7g of water. The resulting damp solid was heated in an air purged oven for 4 hours during which time the oven temperature was raised from 100° to 300° C at a rate of 0.8° C $min^{-1}$.

This water-treated sample of catalyst was again tested as in Example 1. A selectivity to ethylene oxide of 92% was obtained.

We claim:

1. A process of restoring selectivity to unstable silver containing catalysts promoted with an alkali metal selected from the group consisting of sodium, potassium, rubidium and cesium for the oxidation of olefines to olefine oxides which have lost selectivity in that reaction, which comprises wetting the catalyst with water and drying it.

2. A process as claimed in claim 1 in which the amount of water absorbed into the catalyst is substantially equal to the water porosity of the catalyst.

3. A process as claimed in claim 1 in which the catalyst comprises silver and an alkali metal component supported on a porous heat resisting support and in which the silver is present as particles at least 50% of which are discrete particles adhering to the support and having equivalent diameters of less than 10,000A.

4. A process as claimed in claim 3 in which the support is alpha-alumina.

5. A process as claimed in claim 3 in which the silver and alkali metal have been introduced to the support by impregantion.

6. A process as claimed in claim 5 in which the catalyst is formed by impregnating a preformed porous heat resisting support with a solution comprising 3-50% of silver by weight and a nitrogen containing ligand.

7. A process as claimed in claim 3 in which the support has a surface area in the range 0.04 to 10 $m^2/g$ as measured by the Brunauer, Emmett and Teller method, an apparent porosity as measured by the mercury absorption method of at least 20% and median pore diameters of 0.3 to 15 microns as measured by the mercury porosimetry method, and the catalyst comprises 3-15% by weight of silver.

8. A process as claimed in claim 1 in which the catalyst is substantially free from alkaline earth metal.

9. A process as claimed in claim 7 in which the catalyst comprises a content of sodium in the range $3 \times 10^{-5}$ to $5 \times 10^{-1}$ $g/m^2$ of surface area of the support, a content of potassium in the range $2 \times 10^{-2}$ to $3 \times 10^{-5}$ $g/m^2$ of surface area of the support, a content of rubidium in the range $1 \times 10^{-2}$ to $3 \times 10^{-5}$ $g/m^2$ of the surface area of the support or a content of cesium in the range $5 \times 10^{-3}$ to $3 \times 10^{-5}$ $g/m^2$ of surface area of the support, expressed as the weight of the element.

10. A process which comprises producing an olefine oxide by contacting an olefine with oxygen in the presence of an unstable silver containing catalyst promoted with an alkali metal selected from the group consisting of sodium, potassium, rubidium and cesium in which the selectivity of the catalyst is restored by wetting the catalyst with water and drying it.

11. A process as claimed in claim 1 in which the alkylene oxide is ethylene oxide.

* * * * *